(12) United States Patent
Flick (10) Patent No.: US 10,247,443 B2
(45) Date of Patent: Apr. 2, 2019

(54) ELECTRICALLY OPERATED AEROSOL GENERATING SYSTEM HAVING AEROSOL PRODUCTION CONTROL

(71) Applicant: Philip Morris Products S.A., Neuchatel (CH)

(72) Inventor: Jean-Marc Flick, Pomy (CH)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 513 days.

(21) Appl. No.: 14/354,316

(22) PCT Filed: Oct. 25, 2012

(86) PCT No.: PCT/EP2012/071169
§ 371 (c)(1),
(2) Date: Apr. 25, 2014

(87) PCT Pub. No.: WO2013/060784
PCT Pub. Date: May 2, 2013

(65) Prior Publication Data
US 2014/0321837 A1    Oct. 30, 2014

(30) Foreign Application Priority Data

Oct. 27, 2011 (EP) .................................. 11250874

(51) Int. Cl.
*A01G 13/06* (2006.01)
*A61M 15/00* (2006.01)
(Continued)

(52) U.S. Cl.
CPC .......... *F24H 1/0018* (2013.01); *A24F 47/008* (2013.01); *A61M 11/042* (2014.02);
(Continued)

(58) Field of Classification Search
CPC ... A24F 47/008; A61M 11/042; A61M 15/06; A61M 2016/0024; A61M 2205/3653;
(Continued)

(56) References Cited

U.S. PATENT DOCUMENTS 3,128,764 A * 4/1964 Koehn ................... A61M 16/18
128/203.25
3,584,621 A * 6/1971 Bird ....................... A61M 16/00
128/200.18
(Continued)

FOREIGN PATENT DOCUMENTS

CN    101518361 A    9/2009
CN    101557728 A    10/2009
(Continued)

OTHER PUBLICATIONS

Combined Taiwanese Office Action and Search Report dated Nov. 16, 2015 in Patent Application No. 101139223 (English language translation only).
(Continued)

*Primary Examiner* — Dana Ross
*Assistant Examiner* — Ket D Dang
(74) *Attorney, Agent, or Firm* — Oblon, McClelland, Maier & Neustadt, L.L.P.

(57) ABSTRACT

A method of controlling aerosol production in an aerosol-generating device is provided, the device including a powered aerosol generating element, a flow channel to allow a flow of gas past the element, and a flow sensor to detect air flow in the flow channel, the method including: determining a value of a first parameter related to a change in flow rate; and reducing a supply of power to the element depending on a comparison result between the first parameter value and a threshold value, the first parameter being derived from a combination of a second parameter that is a measure of a
(Continued)

flow rate detected by the flow sensor and a third parameter related to the flow rate. Also provided is a method of reducing or suspending aerosol production, based not simply on a detected flow rate, but on another measure indicative of the evolution of the flow characteristics.

12 Claims, 5 Drawing Sheets

(51) Int. Cl.

| | |
|---|---|
| *F24H 1/00* | (2006.01) |
| *A24F 47/00* | (2006.01) |
| *A61M 15/06* | (2006.01) |
| *A61M 11/04* | (2006.01) |
| *F24H 9/20* | (2006.01) |
| *A61M 16/00* | (2006.01) |

(52) U.S. Cl.
CPC ........... *A61M 15/06* (2013.01); *F24H 9/2014* (2013.01); *A61M 2016/0024* (2013.01); *A61M 2205/3653* (2013.01); *A61M 2205/8206* (2013.01)

(58) Field of Classification Search
CPC .......... A61M 2205/8206; F24H 1/0018; F24H 9/2014
USPC ............... 392/387, 394; 128/203.12–203.15, 128/203.19, 203.21, 203.23, 203.27, 128/204.23, 204.26, 205.24, 200.14, 128/200.23, 204.21, 205.23, 204.17; 137/487.5; 251/304; 131/200, 194, 273, 131/331, 359, 360; 239/338, 102.2
See application file for complete search history.

(56) References Cited

U.S. PATENT DOCUMENTS

| | | | | |
|---|---|---|---|---|
| 5,095,921 | A | 3/1992 | Losee et al. | |
| 5,372,148 | A | 12/1994 | McCafferty et al. | |
| 5,704,345 | A * | 1/1998 | Berthon-Jones ....... | A61B 5/087 128/204.21 |
| 5,970,973 | A * | 10/1999 | Gonda .................. | A61K 9/007 128/200.14 |
| 6,040,560 | A | 3/2000 | Fleischhauer et al. | |
| 6,234,167 | B1 * | 5/2001 | Cox .................. | A61M 15/0065 128/200.14 |
| 6,540,154 | B1 * | 4/2003 | Ivri ...................... | A61M 11/005 239/102.2 |
| 6,584,971 | B1 | 7/2003 | Denyer et al. | |
| 6,675,797 | B1 * | 1/2004 | Berthon-Jones ....... | A61B 5/087 128/204.18 |
| 6,971,383 | B2 | 12/2005 | Hickey et al. | |
| 7,106,955 | B2 | 9/2006 | Thudor et al. | |
| 2003/0033055 | A1 * | 2/2003 | McRae ................ | A61M 11/041 700/266 |
| 2003/0136400 | A1 * | 7/2003 | Klimowicz ........... | A61M 15/00 128/200.16 |
| 2003/0140921 | A1 | 7/2003 | Smith et al. | |
| 2004/0079368 | A1 * | 4/2004 | Gupta .................. | A61M 11/041 128/203.12 |
| 2004/0081624 | A1 * | 4/2004 | Nguyen ............... | A61K 9/0078 424/44 |
| 2004/0223917 | A1 * | 11/2004 | Hindle .................. | A61K 9/007 424/45 |
| 2005/0076906 | A1 * | 4/2005 | Johnson ........... | A61M 16/0051 128/204.21 |
| 2006/0047368 | A1 * | 3/2006 | Maharajh ................. | F22B 1/28 700/283 |
| 2006/0193611 | A1 * | 8/2006 | Ruiz Ballesteros .... | A61L 9/037 392/394 |
| 2007/0125370 | A1 | 6/2007 | Denyer et al. | |
| 2008/0092912 | A1 | 4/2008 | Robinson et al. | |
| 2010/0024816 | A1 | 2/2010 | Weinstein et al. | |
| 2010/0071698 | A1 * | 3/2010 | Kiritake ............. | A61M 16/009 128/205.27 |
| 2010/0116270 | A1 * | 5/2010 | Edwards ............ | A61M 16/127 128/201.21 |
| 2010/0200006 | A1 | 8/2010 | Robinson et al. | |
| 2010/0242974 | A1 | 9/2010 | Pan | |
| 2011/0017211 | A1 | 1/2011 | Ahlmén et al. | |
| 2011/0155133 | A1 * | 6/2011 | Barnes ................. | A61M 16/00 128/204.21 |
| 2012/0060853 | A1 | 3/2012 | Robinson et al. | |
| 2012/0186594 | A1 | 7/2012 | Liu | |

FOREIGN PATENT DOCUMENTS

| | | | | |
|---|---|---|---|---|
| CN | 102227175 A | 10/2011 | | |
| EP | 0 488 488 | 6/1992 | | |
| EP | 1 092 446 A2 | 4/2001 | | |
| EP | 2 083 643 A1 | 8/2009 | | |
| GB | 2 343 122 A | 5/2000 | | |
| JP | 2005-34021 A | 2/2005 | | |
| RU | 2 311 859 C2 | 12/2007 | | |
| RU | 2 425 608 C2 | 8/2011 | | |
| WO | WO 9207599 A1 * | 5/1992 | ........... | A61M 15/00 |
| WO | WO 2004/080216 A1 | 9/2004 | | |
| WO | WO 2009/013504 A2 | 1/2009 | | |
| WO | WO 2009/132793 A1 | 11/2009 | | |
| WO | 2011 033396 | 3/2011 | | |
| WO | WO 2011/050964 A1 | 5/2011 | | |

OTHER PUBLICATIONS

The Extended European Search Report dated Jul. 3, 2012, in Application No. / Patent No. 11250874.2-2313.
International Preliminary Report on Patentability dated Apr. 29, 2014, in International Application No. PCT/EP2012/071169.
Written Opinion of the International Searching Authority dated Apr. 19, 2013 in PCT/EP12/071169 Filed Oct. 25, 2012.
International Search Report dated Apr. 19, 2013 in PCT/EP12/071169 Filed Oct. 25, 2012.
Office Action dated Jun. 15, 2016 in Japanese Patent Application No. 2014-537618 (submitting English language translation only).
Combined Office Action and Search Report dated Sep. 6, 2015 in Chinese Patent Application No. 201280055759.9 (submitting English language translation only).
Office Action dated Aug. 24, 2016 in Russian Patent Application No. 2014121237 (submitting English language translation only).
Examination Report dated Sep. 28, 2016 in GCC Patent Application No. GC 2012-22825.
Grant dated Jun. 15, 2016 in Kazak Patent Application No. 31266.
European Opposition dated Jan. 27, 2017 in Patent Application No. 11250874.2 (Patent No. EP 2 770 860 B1).

* cited by examiner

ELECTRICALLY OPERATED AEROSOL GENERATING SYSTEM HAVING AEROSOL PRODUCTION CONTROL

CROSS REFERENCE TO RELATED APPLICATION

This application is a national phase application based on PCT/EP2012/071169, filed on Oct. 25, 2012.

TECHNICAL FIELD

The present invention relates to a method for controlling aerosol production. The present invention further relates to an aerosol generating system and more specifically to an electrically operated aerosol generation system. The present invention finds particular application as a method for controlling aerosol production in an aerosol generation system through at least one electric element of an electrically operated smoking system.

DESCRIPTION OF RELATED ART

WO-A-2009/132793 discloses an electrically heated smoking system. A liquid is stored in a liquid storage portion, and a capillary wick has a first end which extends into the liquid storage portion for contact with the liquid therein, and a second end which extends out of the liquid storage portion. A heating element heats the second end of the capillary wick. The heating element is in the form of a spirally wound electric heating element in electrical connection with a power supply, and surrounding the second end of the capillary wick. In use, the heating element may be activated by the user to switch on the power supply. Suction on a mouthpiece by the user causes air to be drawn into the electrically heated smoking system over the capillary wick and heating element and subsequently into the mouth of the user.

It is an objective of the present invention to provide an improved method of controlling the electric heating element of such an electrically heated aerosol generating system.

One particular problem with an aerosol generating devices is condensation of the aerosol inside the device. The aerosol can condense into a liquid within the aerosol condensation chamber and the liquid can then leak out of the device. In particular, for aerosol generation devices used for inhalation, the liquid in the aerosol condensation chamber could leak while the device is not in use or while the device is in use, entering a user's mouth. Any liquid which enters the user's mouth could be unpleasant and potentially hazardous.

A further problem with condensation within aerosol generating devices is that the condensates of the aerosol can migrate or settle onto the aerosol generating element and interfere with its operation. In the case of thermal vaporization, if an aerosol condensate is subsequently re-evaporated this can lead to chemical degradation of the original liquid formulation. This could result in an unpleasant taste or hazardous chemicals.

It would be desirable to minimise condensation of aerosols generated by, and within, such aerosol generating devices.

SUMMARY

According to one aspect of the invention, there is provided a method of controlling aerosol production in an aerosol-generating device, the device comprising:

an aerosol generating element;
a flow channel configured to allow an air flow past the aerosol generating element;
and a flow sensor configured to detect the air flow in the flow channel, comprising the steps of:
determining a value of a first parameter related to a change in flow rate of the air flow; and
changing the supply of power to the aerosol generating element depending on a result of a comparison between the value of the first parameter and a threshold value, wherein the first parameter is derived from a combination of a second parameter that is a measure of a flow rate detected by the flow sensor and a third parameter related to the flow rate,
and wherein the third parameter is temperature, power supplied to the aerosol generating element, a maximum detected flow rate, or a rate of change of flow rate, or is derived from a combination of two or more of temperature, power supplied to the aerosol generating element, a maximum detected flow rate, and a rate of change of flow rate.

Preferably, the device is configured to allow the air flow to be generated by a user inhalation. Preferably, the step of determining comprises determining a value of the first parameter during an inhalation period. Preferably the step of changing the power supply comprises reducing the supply of power to zero.

An aerosol is a suspension of solid particles or liquid droplets in a gas, such as air. By controlling the power supplied to the aerosol generating element, the rate of aerosol generation can be controlled. By reducing or suspending power to the aerosol generating element before the end of a period of air flow, such as a user inhalation or puff, the remaining portion of the air flow can be used to remove or purge already generated aerosol, and thus reduce condensation within the device. However, the most desirable time to stop aerosol generation depends on the rate and variance of the air flow during a defined period. For a device driven by user inhalation, different users have different inhalation behaviour, and a single user can have different inhalation behaviour at different times. So it is desirable to have a control method that compensates for or normalises between different user behaviours. A set flow rate threshold for controlling aerosol production does not work equally well in removing produced aerosol for short sharp user inhalations and long slow inhalations. A flow threshold appropriate for a short sharp inhalation may never be reached by a user taking long slow inhalations.

Preferably, the present invention provides a method of controlling aerosol production, and in particular reducing or suspending aerosol production, based on a detected flow rate and on another measure called the first parameter which is indicative of the evolution of the flow characteristics of the air flow. However, it does not have to be only the detected flow rate, but could be based on different puff parameters.

The second parameter may be a parameter that does not have units of flow rate but is nevertheless a measure of flow rate. For example, the flow sensor may operate by determining the resistance of an electrical filament in the air flow, and so the second parameter may be a resistance value rather than a flow rate calculated from a resistance value. In other words the second parameter may be a parameter having a constant relationship with flow rate rather than the actual flow rate. The invention does not require an actual flow rate to be calculated.

If the third parameter is temperature or maximum flow rate, then advantageously the first parameter is proportional to a ratio between the second and third parameters.

If the third parameter is power supplied to the aerosol generating element or rate of change of flow rate, the first parameter is advantageously proportional to a product of the second and third parameters.

Alternatively, the first parameter may simply be proportional to a rate of change of flow rate.

However, many possibilities exist for the first parameter. The most appropriate first parameter depends on the design of the aerosol-generating device. Different designs may have different flow characteristics past a flow sensor, and different types of aerosol-generating devices may behave differently. Although the preferred examples are simple products or ratios of two detected or derived parameters, more complex combinations may be used.

The aerosol generating element may be a mechanical device, such as a vibrating orifice transducer or a piezoelectric device. However, preferably, the aerosol generating element is an electrical heater comprising at least one heater element. The at least one electric heating element may be arranged to heat an aerosol-forming substrate to form the aerosol.

If a constant power is provided to the heating element, the temperature of the heating element is a parameter that is indicative of the flow characteristics within the device. This may be used as the third parameter. For lower temperatures there is a high flow rate as the air flow provides a cooling effect. So, the temperature of the heating element will increase as the flow rate drops at the end of a user inhalation. The resistance of the heating element may be dependent on the temperature of the heating element, so that the resistance of the heating element may be used as the third parameter.

If the temperature is controlled to remain constant, then the power supplied to the heater element to maintain a constant temperature is indicative of the flow rate and so may be used as the third parameter. The higher the flow rate the more power is required to maintain a given temperature. The constant temperature may be a predetermined value or may be dynamically calculated based on one or more other measured parameters, such as flow rate.

According to another aspect of the invention, there is provided an electrically operated aerosol generating device, the device comprising: at least one electric aerosol generating element for forming an aerosol from a substrate; a power supply for supplying power to the at least one aerosol generating element; and electric circuitry for controlling supply of power from the power supply to the at least one aerosol generating element, the electric circuitry including a sensor for detecting a air flow past the aerosol generating element and wherein the electric circuitry is arranged to:

determine a value of a first parameter related to a change in flow rate of the air flow; and reduce or suspend the supply of power to the aerosol generating element dependent on a result a comparison between the value of the first parameter and a threshold value, wherein the first parameter is derived from a combination of a second parameter that is a measure of a flow rate detected by the flow sensor and a third parameter related to the flow rate, and wherein the third parameter is temperature, power supplied to the aerosol generating element, a maximum detected flow rate, or a rate of change of flow rate, or is derived from a combination of two or more of temperature, power supplied to the aerosol generating element, a maximum detected flow rate, and a rate of change of flow rate.

Preferably, the device is configured to allow the air flow to be generated by a user inhalation. Preferably, the device is configured to determine a value of the first parameter during an inhalation period.

If the third parameter is temperature or maximum flow rate, then preferably the first parameter is proportional to a ratio between the second and third parameters.

If the third parameter is power supplied to the aerosol generating element or rate of change of flow rate, the first parameter is preferably proportional to a product of the second and third parameters.

Alternatively, the first parameter may simply be proportional to a rate of change of flow rate.

The device may be configured to receive an aerosol-forming substrate. The aerosol generating element may be a mechanical device, such as a vibrating orifice transducer. However, preferably, the aerosol generating element is an electrical heater comprising at least one heater element. The at least one electric heating element may be arranged to heat an aerosol-forming substrate to form the aerosol.

If a constant power is provided to the heating element, the temperature of the heating element is a parameter that is indicative of the flow characteristics within the device. Temperature may then be used as the third parameter. For lower temperatures there is a high flow rate as the air flow provides a cooling effect. So, the temperature of the heating element will increase as the flow rate drops at the end of a user inhalation (or other air flow period). The electrical resistance of the heating element may be dependent on the temperature of the heating element, so that the electrical resistance of the heating element may be used as the third parameter.

If the temperature is controlled to remain constant, then the power supplied to the heater element to maintain a constant temperature is indicative of the flow rate and so may be used as the third parameter. The higher the flow rate the more power is required to maintain a given temperature. The constant temperature may be a predetermined value or may be dynamically calculated based on one or more other measured parameters, such as flow rate.

Preferably, the electric circuitry is arranged to perform the method steps of the previous aspect of the invention. To perform the method steps of the previous aspect of the invention, the electric circuitry may be hardwired. More preferably, however, the electric circuitry is programmable to perform the method steps of the previous aspect of the invention.

The sensor may be any sensor which can detect airflow. The sensor may be an electro-mechanical device. Alternatively, the sensor may be any of: a mechanical device, an optical device, an opto-mechanical device, a micro electro mechanical systems (MEMS) based sensor and an acoustic sensor. The sensor can be a thermal conductive flow sensor, a pressure sensor, an anemometer and should be able to not only detect an airflow but should be able to measure the airflow. So, the sensor should be able to deliver an analogue electrical signal or digital information that is representative of the amplitude of the air flow.

The electric heater may comprise a single heating element. Alternatively, the electric heater may comprise more than one heating element, for example two, or three, or four, or five, or six or more heating elements. The heating element or heating elements may be arranged appropriately so as to most effectively heat the aerosol-forming substrate.

The at least one electric heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Del. 19898, United States of America.

Alternatively, the at least one electric heating element may comprise an infra-red heating element, a photonic source, or an inductive heating element.

The at least one electric heating element may take any suitable form. For example, the at least one electric heating element may take the form of a heating blade. Alternatively, the at least one electric heating element may take the form of a casing or substrate having different electro-conductive portions, or an electrically resistive metallic tube. If the aerosol-forming substrate is a liquid provided within a container, the container may incorporate a disposable heating element. Alternatively, one or more heating needles or rods that run through the centre of the aerosol-forming substrate may also be suitable. Alternatively, the at least one electric heating element may be a disk (end) heater or a combination of a disk heater with heating needles or rods. Alternatively, the at least one electric heating element may comprise a flexible sheet of material arranged to surround or partially surround the aerosol-forming substrate. Other alternatives include a heating wire or filament, for example a Ni—Cr, platinum, tungsten or alloy wire, or a heating plate. Optionally, the heating element may be deposited in or on a rigid carrier material.

The at least one electric heating element may comprise a heat sink, or heat reservoir comprising a material capable of absorbing and storing heat and subsequently releasing the heat over time to the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, metal salt, a mixture of eutectic salts or an alloy.

The heat sink or heat reservoir may be arranged such that it is directly in contact with the aerosol-forming substrate and can transfer the stored heat directly to the substrate. Alternatively, the heat stored in the heat sink or heat reservoir may be transferred to the aerosol-forming substrate by means of a heat conductor, such as a metallic tube.

The at least one heating element may heat the aerosol-forming substrate by means of conduction. The heating element may be at least partially in contact with the substrate, or the carrier on which the substrate is deposited. Alternatively, the heat from the heating element may be conducted to heat conductive element.

Alternatively, the at least one heating element may transfer heat to the incoming ambient air that is drawn through the electrically heated aerosol generating device during use, which in turn heats the aerosol-forming substrate by convection. The ambient air may be heated before passing through the aerosol-forming substrate. Alternatively, if the aerosol-forming substrate is a liquid substrate, the ambient air may be first drawn through the substrate and then heated.

The aerosol-forming substrate may be a solid aerosol-forming substrate. The aerosol-forming substrate preferably comprises a tobacco-containing material containing volatile tobacco flavour compounds which are released from the substrate upon heating. The aerosol-forming substrate may comprise a non-tobacco material. The aerosol-forming substrate may comprise tobacco-containing material and non-tobacco containing material. Preferably, the aerosol-forming substrate further comprises an aerosol former. Examples of suitable aerosol formers are glycerine and propylene glycol.

Alternatively, the aerosol-forming substrate may be a liquid aerosol-forming substrate. In one embodiment, the electrically heated aerosol generating device further comprises a liquid storage portion. Preferably, the liquid aerosol-forming substrate is stored in the liquid storage portion. In one embodiment, the electrically heated aerosol generating device further comprises a capillary wick in communication with the liquid storage portion. It is also possible for a capillary wick for holding liquid to be provided without a liquid storage portion. In that embodiment, the capillary wick may be preloaded with liquid.

Preferably, the capillary wick is arranged to be in contact with liquid in the liquid storage portion. In that case, in use, liquid is transferred from the liquid storage portion towards the at least one electric heating element by capillary action in the capillary wick. In one embodiment, the capillary wick has a first end and a second end, the first end extending into the liquid storage portion for contact with liquid therein and the at least one electric heating element being arranged to heat liquid in the second end. When the heating element is activated, the liquid at the second end of the capillary wick is vaporized by the heater to form the supersaturated vapour. The supersaturated vapour is mixed with and carried in the airflow. During the flow, the vapour condenses to form the aerosol and the aerosol is carried towards the mouth of a user. The heating element in combination with a capillary wick may provide a fast response, because that arrangement may provide a high surface area of liquid to the heating element. Control of the heating element according to the invention may therefore depend on the structure of the capillary wick arrangement.

The liquid substrate may be absorbed into a porous carrier material, which may be made from any suitable absorbent plug or body, for example, a foamed metal or plastics material, polypropylene, terylene, nylon fibres or ceramic. The liquid substrate may be retained in the porous carrier material prior to use of the electrically heated aerosol generating device or alternatively, the liquid substrate material may be released into the porous carrier material during, or immediately prior to use. For example, the liquid substrate may be provided in a capsule. The shell of the capsule preferably melts upon heating and releases the liquid substrate into the porous carrier material. The capsule may optionally contain a solid in combination with the liquid.

If the aerosol-forming substrate is a liquid substrate, the liquid has specific physical properties. These include, for example, a boiling point, vapour pressure, and surface tension characteristics to make them suitable for use in the aerosol generating device. Control of the at least one electric heating element may depend upon the physical properties of the liquid substrate. The liquid preferably comprises a tobacco-containing material comprising volatile tobacco flavour compounds which are released from the liquid upon heating. Alternatively, or in addition, the liquid may comprise a non-tobacco material. The liquid may include water, solvents, ethanol, plant extracts and natural or artificial flavours. Preferably, the liquid further comprises an aerosol former. Examples of suitable aerosol formers are glycerine and propylene glycol.

An advantage of providing a liquid storage portion is that a high level of hygiene can be maintained. Using a capillary wick extending between the liquid and the electric heating element, allows the structure of the device to be relatively simple. The liquid has physical properties, including viscosity and surface tension, which allow the liquid to be transported through the capillary wick by capillary action. The liquid storage portion is preferably a container. The liquid storage portion may not be refillable. Thus, when the liquid in the liquid storage portion has been used up, the liquid storage portion, or the entire aerosol generating device, is replaced. Alternatively, the liquid storage portion may be refillable. In that case, the aerosol generating device may be replaced after a certain number of refills of the liquid storage portion. Preferably, the liquid storage portion is arranged to hold liquid for a pre-determined number of puffs.

The capillary wick may have a fibrous or spongy structure. The capillary wick preferably comprises a bundle of capillaries. For example, the capillary wick may comprise a plurality of fibres or threads, or other fine bore tubes. The fibres or threads may be generally aligned in the longitudinal direction of the aerosol generating device. Alternatively, the capillary wick may comprise sponge-like or foam-like material formed into a rod shape. The rod shape may extend along the longitudinal direction of the aerosol generating device. The structure of the wick forms a plurality of small bores or tubes, through which the liquid can be transported to the electric heating element, by capillary action. The capillary wick may comprise any suitable material or combination of materials. Examples of suitable materials are ceramic- or graphite-based materials in the form of fibres or sintered powders. The capillary wick may have any suitable capillarity and porosity so as to be used with different liquid physical properties such as density, viscosity, surface tension and vapour pressure. The capillary properties of the wick, combined with the properties of the liquid, ensure that the wick is always wet in the heating area.

The aerosol-forming substrate may alternatively be any other sort of substrate, for example, a gas substrate, or any combination of the various types of substrate. During operation, the substrate may be completely contained within the electrically heated aerosol generating device. In that case, a user may puff on a mouthpiece of the electrically heated aerosol generating device. Alternatively, during operation, the substrate may be partially contained within the electrically heated aerosol generating device. In that case, the substrate may form part of a separate article and the user may puff directly on the separate article.

Preferably, the electrically heated aerosol generating device is an electrically heated smoking device.

The electrically heated aerosol generating device may comprise an aerosol-forming chamber in which aerosol forms from a super saturated vapour, which aerosol is then carried into the mouth of the user. An air inlet, air outlet and the chamber are preferably arranged so as to define an airflow route from the air inlet to the air outlet via the aerosol-forming chamber, so as to convey the aerosol to the air outlet and into the mouth of a user. Condensation may form on the walls of the aerosol-forming chamber. The amount of condensation may depend on the amount of power supplied, particularly towards the end of the puff.

Preferably, the aerosol generating device comprises a housing. Preferably, the housing is elongate. The structure of the housing, including the surface area available for condensation to form, will affect the aerosol properties and whether there is liquid leakage from the device. The housing may comprise a shell and a mouthpiece. In that case, all the components may be contained in either the shell or the mouthpiece. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle. The material of the housing may affect the amount of condensation forming on the housing which will, in turn, affect liquid leakage from the device Preferably, the aerosol generating device is portable. The aerosol generating device may be a smoking device and may have a size comparable to a conventional cigar or cigarette. The smoking device may have a total length between approximately 30 mm and approximately 150 mm. The smoking device may have an external diameter between approximately 5 mm and approximately 30 mm.

The method and electrically heated aerosol generating device according to the present invention provide the advantage that the amount of power supplied to the heating element may be tailored to the air flow profile, thereby providing an improved experience for the user and reducing the amount of aerosol that condenses within the housing of the device, without requiring any additional user or device actions.

According to another aspect of the invention, there is provided electric circuitry for an electrically operated aerosol generating device, the electric circuitry being arranged to perform the method of the other aspects of the invention.

Preferably, the electric circuitry is programmable to perform the method of the other aspects of the invention. Alternatively, the electric circuitry may be hardwired to perform the method of the other aspects of the invention.

According to another aspect of the invention, there is provided a computer program which, when run on programmable electric circuitry for an electrically operated aerosol generating device, causes the programmable electric circuitry to perform the method of the other aspects of the invention.

According a another aspect of the invention, there is provided a computer readable storage medium having stored thereon a computer program according to the previous aspect of the invention.

Features described in relation to one aspect of the invention may be applicable to another aspect of the invention.

BRIEF DESCRIPTION OF THE DRAWINGS

The invention will be further described, by way of example only, with reference to the accompanying drawings, in which.

DETAILED DESCRIPTION

Figure 1:
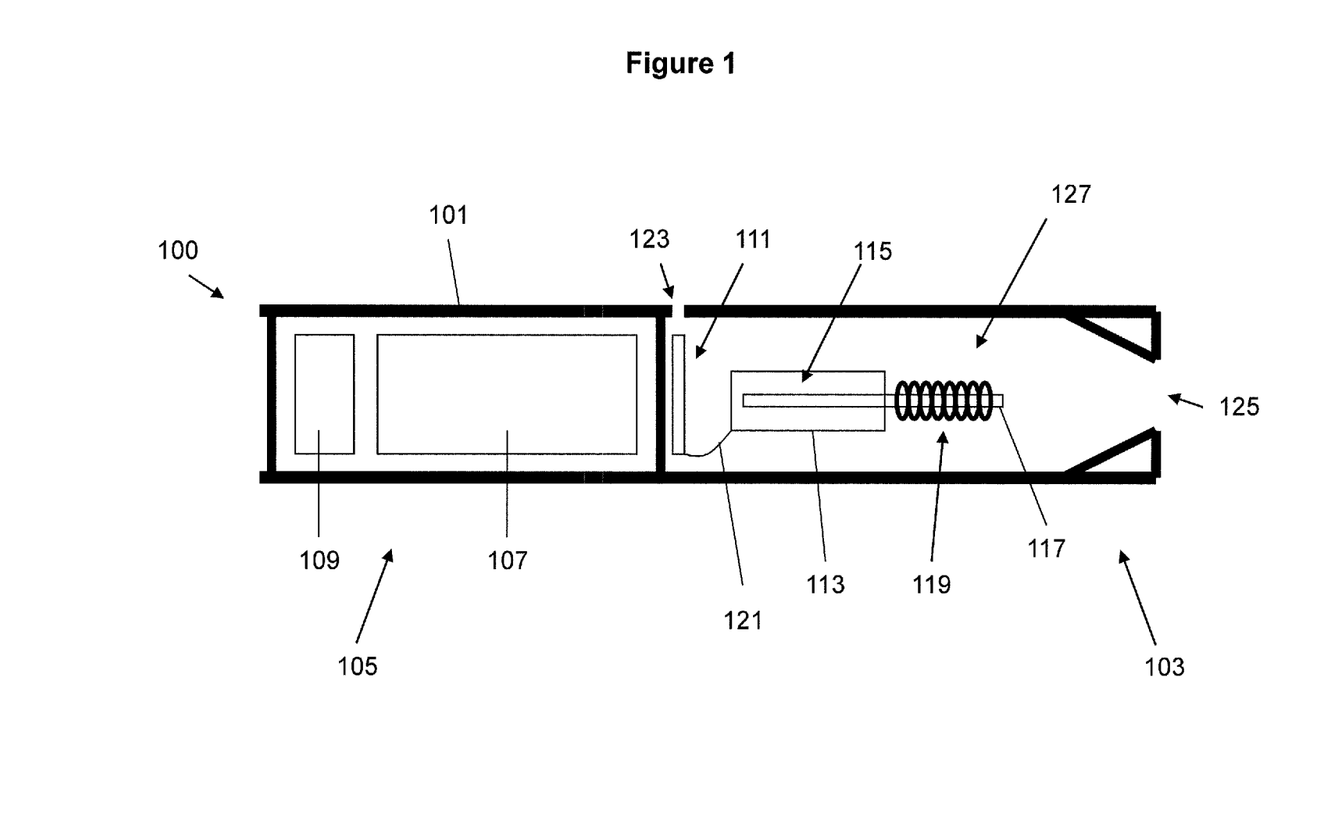
FIG. 1 shows one example of an electrically heated aerosol generating device.

FIG. 1 shows one example of an electrically heated aerosol generating device. In FIG. 1, the device is a smoking device having a liquid storage portion. The smoking device 100 of FIG. 1 comprises a housing 101 having a mouthpiece end 103 and a body end 105. In the body end, there is provided an electric power supply in the form of battery 107 and electric circuitry in the form of hardware 109 and a puff detection device 111. In the mouthpiece end, there is provided a liquid storage portion in the form of cartridge 113 containing liquid 115, a capillary wick 117 and a heater 119 comprising at least one heating element. Note that the heater is only shown schematically in FIG. 1. One end of the capillary wick 117 extends into the cartridge 113 and the other end of the capillary wick 117 is surrounded by the heater 119. The heater is connected to the electric circuitry via connections 121. The housing 101 also includes an air inlet 123, an air outlet 125 at the mouthpiece end and an aerosol-forming chamber 127.

In use, operation is as follows. Liquid 115 is transferred or conveyed by capillary action from the cartridge 113 from the end of the wick 117 which extends into the cartridge to the other end of the wick 117 which is surrounded by the heater 119. When a user draws on the device at the air outlet 125, ambient air is drawn through air inlet 123. In the arrangement shown in FIG. 1, the puff detection device 111 senses the puff and activates the heater 119. The battery 107 supplies energy to the heater 119 to heat the end of the wick 117 surrounded by the heater. The liquid in that end of the wick 117 is vaporized by the heater 119 to create a supersaturated vapour. At the same time, the liquid being vaporized is replaced by further liquid moving along the wick 117 by capillary action. (This is sometimes referred to as "pumping action") The supersaturated vapour created is mixed with and carried in the airflow from the air inlet 123. In the aerosol-forming chamber 127, the vapour condenses to form an inhalable aerosol, which is carried towards the outlet 125 and into the mouth of the user.

The capillary wick can be made from a variety of porous or capillary materials and preferably has a known, predefined capillarity. Examples include ceramic- or graphite-based materials in the form of fibres or sintered powders. Wicks of different porosities can be used to accommodate different liquid physical properties such as density, viscosity, surface tension and vapour pressure. The wick must be suitable so that the required amount of liquid can be delivered to the heating element. The wick and heating element must be suitable so that the required amount of aerosol can be conveyed to the user.

In the embodiment shown in FIG. 1, the hardware 109 and the puff detection device 111 are preferably programmable. The hardware 109 and puff detection device 111 can be used to manage the device operation. This assists with control of the particle size in the aerosol.

FIG. 1 shows one example of an electrically heated aerosol generating device which may be used with the present invention. Many other examples are usable with the invention, however. The electrically heated aerosol generating device simply needs to include or receive an aerosol forming substrate which can be heated by at least one electric heating element, powered by a power supply under the control of electric circuitry. For example, the device need not be a smoking device. For example, the aerosol forming substrate may be a solid substrate, rather than a liquid substrate. Alternatively, the aerosol forming substrate may be another form of substrate such as a gas substrate. The heating element may take any appropriate form. The overall shape and size of the housing could be altered and the housing could comprise a separable shell and mouthpiece. Other variations are, of course, possible.

As already mentioned, preferably, the electric circuitry, comprising hardware 109 and the puff detection device 111, is programmable in order to control the supply of power to the heating element. This, in turn, affects the temperature profile which will affect the density of the aerosol produced. The term "temperature profile" refers to a graphic representation of the temperature of the heating element (or another similar measure, for example, the heat generated by the heating element) over the time taken for a puff. Alternatively, the hardware 109 and the puff detection device 111 may be hardwired to control the supply of power to the heating element. Again, this will affect the temperature profile which will affect the density of the aerosol generated.

Problems arise in an aerosol generating device of the type shown in FIG. 1 if aerosol continues to be generated when there is insufficient airflow through the device to remove the produced aerosol. This results in condensation of the aerosol on the interior of the housing, which may subsequently leak from the device into the user's mouth or hands. It can also lead to a build up of material that might migrate on heating element which can be subsequently be chemically degraded into undesirable compounds. If, for example, power is switched off at the same fixed flow threshold as it is switched on, aerosol will continue to be generated when there is little or no air flow through the device.

Figure 2:
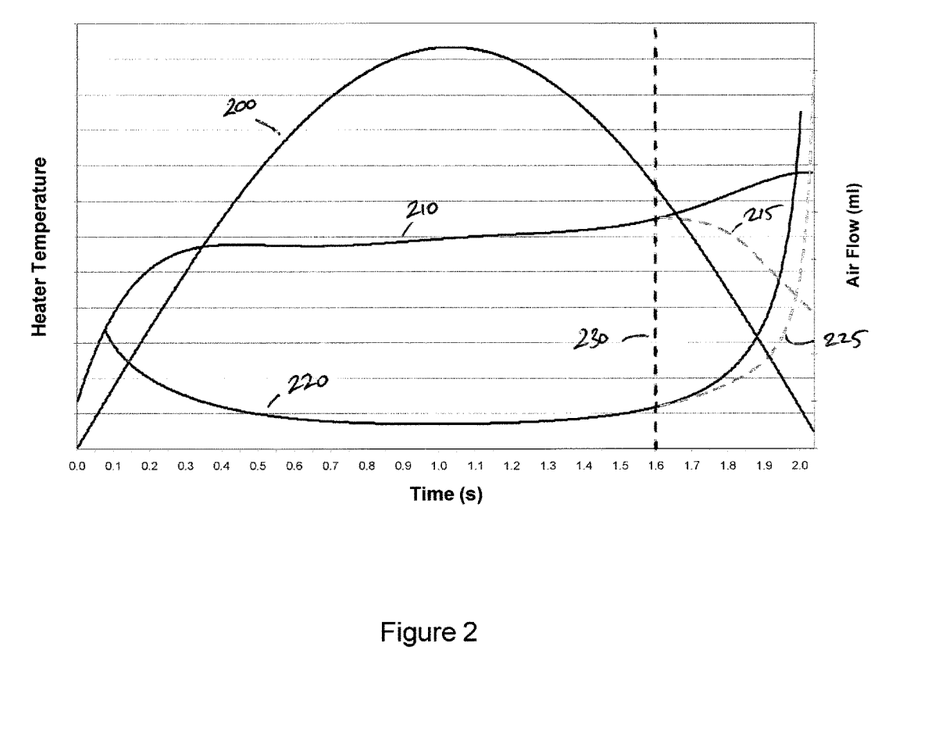
FIG. 2 illustrates a method of controlling aerosol production in accordance with a first embodiment of the invention.

FIG. 2 illustrates a method for controlling power to the heater of FIG. 1 in accordance with a first embodiment of the invention. Curve 200 is the detected air flow through the device during a user inhalation period or puff. Curve 210 is the temperature of the heater during the same period. Power is applied to the heater when air flow through the device is first detected and is continuously applied at the same level until it is switched off. So the temperature of the heater initially rises until it reaches a fairly stable level, at which the cooling of the air flow balances the heating provided by the power supply. Towards the end of the user puff, as air flow is decreasing, the temperature of the heater rises more sharply again. This is because the cooling effect of the air flow is reducing. The heater temperature at is therefore sensitive to a change in air flow during a puff.

Curve 220 is a plot of the temperature of the heater divided by the air flow. This curve is used to provide a normalised threshold for switching off power to the heater and will be referred to as the end of puff variable. The curve 220 is calculated using the following formula:

$$EP = \frac{T}{Q}A \text{ or } EP = \frac{T}{AQ}$$

Where:
EP is the End of puff Variable.
T is the temperature of the heating element.
Q is the Air flow
A is a compensation coefficient.

Power to the heater is stopped when curve 220 reaches a threshold value (but only after the maximum flow rate has passed). In this embodiment the threshold value is preset and stored in the electric circuitry during manufacture. However, it is possible to have a threshold that is changed over time to be most appropriate for a particular user behavior. The power stop is shown by line 230, at 1.6 seconds into the puff. After power is stopped, the temperature of the heater goes down (dotted line 215). The corresponding end of puff variable curve is obtained for the decreasing temperature and is shown in dotted line 225. The threshold is selected so that the temperature of heater decreases enough to significantly reduce the generation of the aerosol up to the end of the puff, but not so early as to frustrate the device user.

Figure 3:
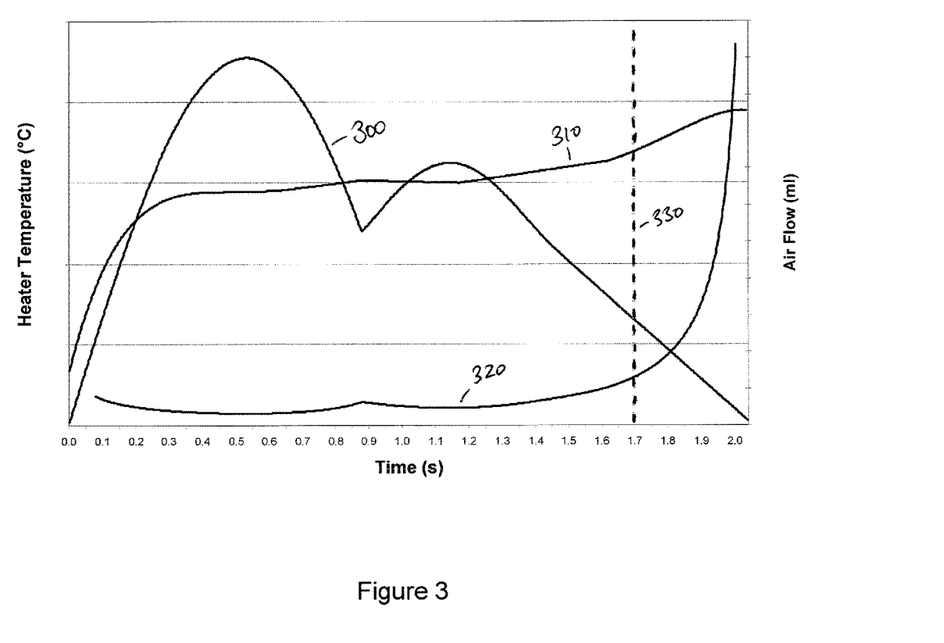
FIG. 3 illustrates a method of controlling aerosol production in accordance with the first embodiment, for a different puff profile.

FIG. 3 shows another example in accordance with the first embodiment, with a more complex flow profile during a puff. Curve 300 shows the air flow, curve 310 shows the heater temperature and curve 320 shows the end of puff variable EP, where:

$$EP = \frac{T}{Q}A$$

Power to the heater is stopped when the end of puff variable reaches the predetermined threshold value, in this case at 1.7 seconds into the puff, shown at line 330.

Reactivation of the heater for subsequent puffs is based on a simple air flow threshold, referred to as the first activation threshold. Once the heating power is stopped, the air flow must go down below the first activation threshold, for the user to be able to take another puff and for the device to be reinitialized.

The temperature of the heating element can be calculated from its electrical resistance, which is continuously measured. Therefore the temperature variable can be replaced by the electrical resistance value of the heating element in the calculation of the end of puff variable, reducing the calculation load for the electric circuitry.

If the temperature of the heater is regulated during a puff, such that it is held constant once it has reached the desired temperature, heater temperature can not be used in calculated the end of puff variable due to the fact that it will remain constant, independently of the air flow level. Therefore another variable input must be used. The power supplied in order to maintain a constant temperature may be used in calculating the end of puff variable. As air flow drops less power is required to maintain the temperature constant.

Power is supplied to the heater in the form of a pulsed signal. In order to regulate the temperature of the heater, the power voltage is modulated. The power voltage modulation can be done by either varying the width of the power voltage pulses or by varying the frequency of the pulses.

The average power that is applied to the heating element can be varied by changing the frequency (or "PFM"—pulse frequency modulation) of the modulations of the power voltage at fixed duty cycle to keep constant the temperature of the heating element. In that case the end of puff variable may be calculated as:

$$EP = \frac{(1 + \Delta f)}{Q}P$$

Where:
Q is the Air flow
$\Delta f$ is the variation of the modulation frequency
P is a compensation coefficient The other way of altering the power applied is PWM (pulse width modulation), which consists of varying the duty cycle at constant frequency. The duty cycle is the ratio of the time that the power is switched on to the time the power is switched off. In other words, the ratio of the width of the voltage pulses to the time between the voltage pulses. A low duty cycle of 5% will provide much less power than a duty cycle of 95%. In that case the end of puff variable may be calculated as:

$$EP = \frac{(1 + \Delta d)}{Q}B$$

Where:
Q is the Air flow
$\Delta d$ is the variation of the duty cycle
B is a compensation coefficient A combination of the frequency and the duty cycle variation can also be used in a calculation of the end of puff variable.

There are several alternative ways of providing a "normalized" parameter to compare with a threshold for stopping power to the heater or any alternative aerosol generating element. One alternative is the use of the rate of change of air flow.

Figure 4:
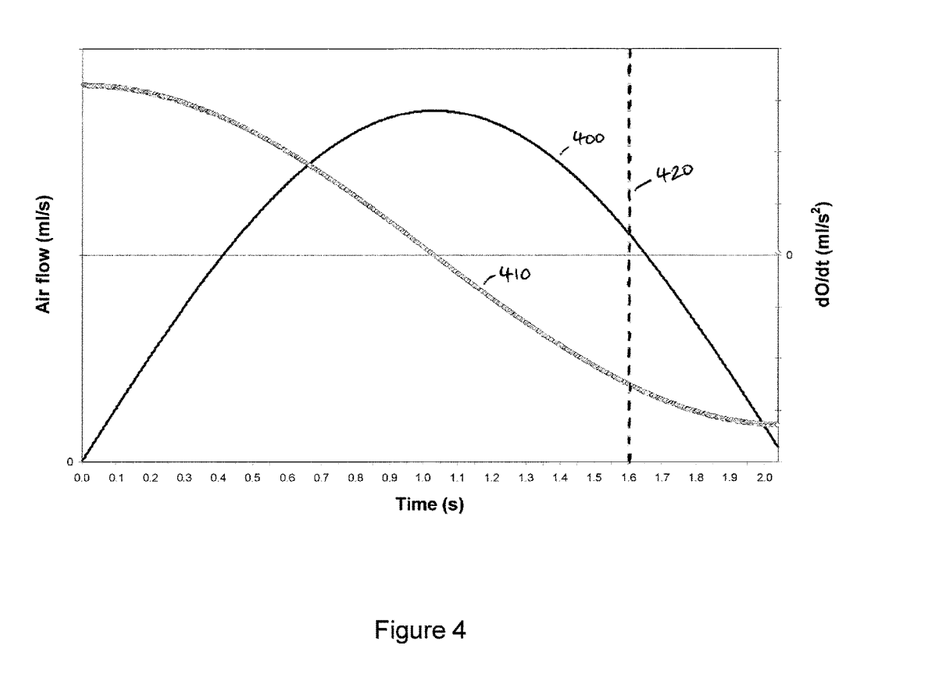
FIG. 4 illustrates a method of controlling aerosol production in accordance with a second embodiment of the invention.

FIG. 4 shows the air flow and the rate of change of air flow for a first puff profile. Curve 400 is the air flow rate. Curve 410 is the derivation of the air flow with respect to time. The threshold for stopping power to the heater can be set at a fixed rate of change of air flow, as illustrated by line 420. The rate of change of air flow normalizes between large and small inhalations.

Figure 5:
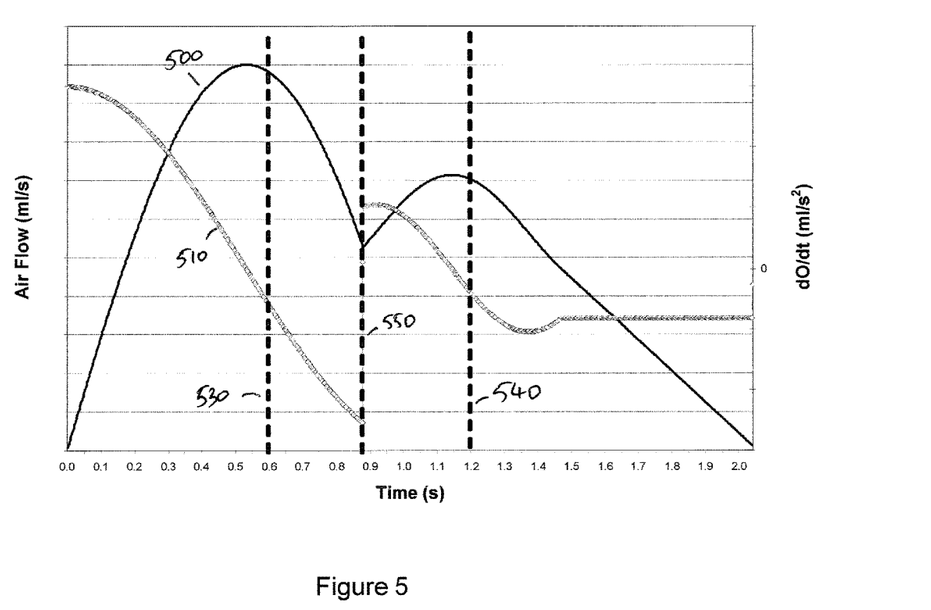
FIG. 5 illustrates a method of controlling aerosol production in accordance with the second embodiment, for a different puff profile.

FIG. 5 shows the use of rate of change or air flow for a more complex puff profile. Curve 500 is the air flow rate and curve 510 is the rate of change of air flow. The power to the heater is stopped when the rate of change of air flow reaches a threshold value. With the puff shown in FIG. 5 the heating power stop will happen several times during the puff, as shown by line 530 and 540. The first power stop occurs after 0.6 s. the second power stop will appear after 1.2 s.

The device needs to be reactivated after the first power stop in order to avoid frustrating the user. The reactivation threshold can take place at the discontinuity of the derivation curve 550 or when the rate of change of air flow goes positive. Once the air flow falls below the first activation threshold, the device can be reset to provide power again when the air flow exceeds the first activation threshold.

The rate of change of air flow can be calculated using the formula.

$$\frac{dQ}{dt} = \frac{(Q_n - Q_{n-1})}{(t_n - t_{n-1})}$$

Where $Q_n$ is the air flow measured at time $t_n$.

Other alternative end of puff parameters include $Q_{max}/Q$, where $Q_{max}$ is the maximum detected air flow during a puff, $A/(Q.dQ/dt)$, $AQ_{max}/(Q.dQ/dt)$ or $AT/Q^2$. For different designs of aerosol generating device, and different users, different end of puff parameters may be appropriate. Whichever end of puff parameter is used it should normalize in some way the different kinds of flow profiles found in user inhalations. This means using a parameter related to the change in air flow over a particular flow period and, as can be seen from the example above, that parameter may be derived from one, two or more detected parameters relating to air flow. The threshold should be set to ensure that the last portion of a user inhalation is used to remove generated aerosol from the device.

Although the invention has been described with reference to an electric smoking device, all aerosol generators, vaporizers or inhalers activated on demand suffer from the same problem of having part of the generated aerosol trapped in the consumable housing. According the present invention can be applied to all aerosol generators, vaporizers or inhalers activated on demand.

In case of medical devices, if the medication dose delivered to the patient has to be estimated and counted, then controlling aerosol production in accordance with the present invention can ensure that all of the generated aerosol is delivered to the patient. By stopping aerosol production before the end of an inhalation substantially all of the aerosol is delivered to the patient and so medication dosage can be more accurately monitored.

Although the invention has been described with reference to electrically heated aerosol-forming substrates, other types of aerosol generator can be used with the present invention. For example, a vibrating orifice transducer may be used to generate aerosol. With such an aerosol generator, the temperature variable used with the heater to calculate the end of puff variable can be replaced by an actuator pressure, power, frequency or amplitude of displacement variables.

The invention claimed is:

1. A method of controlling aerosol production in an aerosol-generating device,
   the device comprising:
      an aerosol-generating element;
      a flow channel configured to allow an air flow past the aerosol-generating element; and
      a flow sensor configured to detect the air flow in the flow channel; and
   the method comprising:
      calculating during a user inhalation, a first value, which is indicative of air flow characteristics of the air flow past the aerosol-generating element; and
      reducing or suspending an amount of power supplied to the aerosol-generating element depending on a result of a comparison between the calculated first value and a threshold value for the reducing or suspending of the amount of the power supplied,
   wherein the threshold value for the reducing or suspending of the amount of the power supplied is set so as to ensure that a last portion of the user inhalation is used to remove generated aerosol from the aerosol-generating device, and
   wherein the first value is calculated from a measure of a flow rate of the air flow detected by the flow sensor and is a rate of change of the air flow, or the method comprises calculating the first value by calculating:
      a ratio between the measure of the flow rate of the air flow detected by the flow sensor and a temperature, or
      a ratio between the measure of the flow rate of the air flow detected by the flow sensor and a maximum detected flow rate, or
      a product of the measure of the flow e of the air flow detected by the flow sensor and the amount of power supplied to the aerosol-generating element, or
      a product of the measure of the flow rate of the air flow detected by the flow sensor and the rate of change of the flow rate of the air flow.

2. The method according to claim 1, wherein the method comprises calculating the first value by calculating the ratio between the measure of the flow rate of the air flow detected by the flow sensor and the temperature or the maximum detected value of the flow rate of the air flow.

3. The method according to claim 1, wherein the method comprises calculating the first value by calculating the product of the measure of the flow rate of the air flow detected by the flow sensor and the amount of power supplied to the aerosol-generating element or the rate of change of the flow rate of the air flow.

4. The method according claim 1, wherein the first value is the rate of change of the flow rate of the air flow.

5. The method according claim 1, wherein the aerosol-generating element is an electrically heated heating element, and the first value is proportional to a temperature of the heating element divided by the flow rate of the air flow detected by the flow sensor.

6. The method according to claim 1, further comprising re-supplying power to the aerosol-generating element based on the flow rate of the air flow detected by the flow sensor.

7. The method according to claim 1, wherein the first value and the threshold value are variable as a function of time.

8. The method according to claim 1, wherein the threshold value is fixed at a constant value.

9. An electrically operated aerosol-generating device, comprising:
   at least one electric aerosol-generating element configured to form an aerosol from a substrate;
   a power supply configured to supply power to the at least one aerosol-generating element; and
   electric circuitry configured to control an amount of power supplied from the power supply to the at least one aerosol-generating element, the electric circuitry including a sensor configured to detect air flow past the aerosol-generating element, wherein the electric circuitry is configured to:
      calculate, during an inhalation period, a first value, which is indicative of air flow characteristics of the air flow past the aerosol-generating element; and
      reduce or suspend the amount of power supplied to the aerosol-generating element to zero dependent on a result of a comparison between the calculated first value and a threshold value for the reducing or the suspending of the amount of the power supplied, wherein the threshold value for the reducing or the suspending of the amount of the power supplied is set so as to ensure that a last portion of a user inhalation is used to remove generated aerosol from the aerosol-generating device, and wherein the first value is calculated from a measure of a flow rate of the air flow detected by the flow sensor and is a rate of change of the air flow, or the method comprises calculating the first value by calculating:

a ratio between the measure of the flow rate of the air flow detected by the flow sensor and a temperature, or a ratio between the measure of the flow rate of the air flow detected by the flow sensor and a maximum detected flow rate, or a product of the measure of the flow rate of the air flow detected by the flow sensor and the amount of power supplied to the aerosol-generating element, or a product of the measure of the flow rate of the air flow detected by the flow sensor and the rate of change of the flow rate of the air flow.

10. The electrically operated aerosol-generating device according to claim 9, wherein the aerosol-generating element is an electrically heated heating element, and the first value is proportional to a temperature of the electrically heated heating element divided by the flow rate of the air flow detected by the flow sensor.

11. Electric circuitry for an electrically operated aerosol-generating device, the electric circuitry being configured to perform a method of controlling aerosol production in the device, the device comprising an aerosol-generating element, a flow channel configured to allow an air flow past the aerosol-generating element, and a flow sensor configured to detect the air flow in the flow channel, the method comprising:

calculating, during an inhalation period, a first value, which is indicative of air flow characteristics of the air flow past the aerosol-generating element; and reducing or suspending an amount of power supplied to the aerosol-generating element depending on a result of a comparison between the calculated first value and a threshold value for the reducing or suspending of the amount of the power supplied, wherein the threshold value for the reducing or suspending the amount of the power supplied is set so as to ensure that a last portion of a user inhalation is used to remove generated aerosol from the aerosol-generating device, and wherein the first value is calculated from a measure of a flow rate of the air flow detected by the flow sensor and is a rate of change of the air flow, or the method comprises calculating the first value by calculating:

a ratio between the measure of the flow of the air flow detected by the flow sensor and a temperature, or a ratio between the measure of the flow rate of the air flow detected by the flow sensor and a maximum detected flow rate, or a product of the measure of the flow rate of the air flow detected by the flow sensor and the amount of power supplied to the aerosol-generating element, or a product of the measure of the flow rate of the air flow detected by the flow sensor and the rate of change of the flow rate of the air flow.

12. A non-transitory computer readable storage medium having a computer program stored thereon, which when run on programmable electric circuitry for an electrically operated aerosol-generating device, causes the programmable electric circuitry to perform a method of controlling aerosol production in the device, the device comprising an aerosol-generating element, a flow channel configured to allow an air flow past the aerosol-generating element, and a flow sensor configured to detect the air flow in the flow channel, the method comprising:

determining a first value, during an inhalation period which is indicative of air flow characteristics of the air flow past the aerosol-generating element; and reducing or suspending an amount of power supplied to the aerosol-generating element depending on a result of a comparison between the determined first value and a threshold value for the reducing or suspending of the amount of the power supplied, wherein the threshold value for the reducing or suspending of the amount of the power supplied is set so as to ensure that a last portion of a user inhalation is used to remove generated aerosol from aerosol-device, and wherein the first value is calculated from a measure of a flow rate of the air flow detected by the flow sensor and is a rate of change of the air flow, or the method comprises calculating the first value by calculating:

a ratio between the measure of the flow rate of the air flow detected by the flow sensor and a temperature, or a ratio between the measure of the flow rate of the air flow detected by the flow sensor and a maximum detected flow rate, or a product of the measure of the flow rate of the air flow detected by the flow sensor and the amount of power supplied to the aerosol-generating element, or a product of the measure of the flow rate of the air flow detected by the flow sensor and the rate of change of the flow rate of the air flow.

* * * * *

UNITED STATES PATENT AND TRADEMARK OFFICE
CERTIFICATE OF CORRECTION

PATENT NO. : 10,247,443 B2
APPLICATION NO. : 14/354316
DATED : April 2, 2019
INVENTOR(S) : Jean-Marc Flick Page 1 of 1

It is certified that error appears in the above-identified patent and that said Letters Patent is hereby corrected as shown below:

In the Claims

At Column 15, Lines 10-11, Claim 9: delete "the method comprises calculating the first value".

Signed and Sealed this
Ninth Day of June, 2020

Andrei Iancu
*Director of the United States Patent and Trademark Office*